United States Patent [19]

Anzeveno et al.

[11] Patent Number: 4,880,917

[45] Date of Patent: Nov. 14, 1989

[54] PROCESS FOR HYDROLYZING 2,6-DIDEOXY-2,6-IMINOHEPTONONITRILE DERIVATIVES USING TRIFLUOROACETIC ACID AND DINITROGEN TETROXIDE

[75] Inventors: Peter B. Anzeveno, Zionsville; John K. Daniel; Laura J. Creemer, both of Indianapolis, all of Ind.; Paul S. Liu, Cincinnati, Ohio

[73] Assignee: Merrell Dow Pharmaceuticals Inc., Cincinnati, Ohio

[21] Appl. No.: 214,229

[22] Filed: Jul. 1, 1988

[51] Int. Cl.$^4$ .................. C07H 15/00; C07H 17/00; C07H 17/02
[52] U.S. Cl. .................................. 536/17.4; 536/17.9
[58] Field of Search ........................ 536/17.4, 17.9

[56] References Cited

U.S. PATENT DOCUMENTS 4,634,765  1/1987  Liu ..................................... 536/17.4
4,639,436  1/1987  Junge et al. .......................... 514/24

Primary Examiner—Morton Foelak
Assistant Examiner—Frederick Krass
Attorney, Agent, or Firm—John J. Kolano

[57] ABSTRACT

A procedure for the mild conversion of a carbonitrile to the corresponding carboxylic acid by first using trifluoroacetic acid in the presence of a catalytic amount of mercuric ion followed by oxidative hydrolysis with dinitrogen tetroxide is described herein. The use of this procedure in the preparation of 1,3,4,5-tetra-O-benzoyl-2,6-dideoxy-2,6-imino-D-glycero-L-gulo-heptitol hydrochloride is also described here.

5 Claims, No Drawings

PROCESS FOR HYDROLYZING 2,6-DIDEOXY-2,6-IMINOHEPTONONITRILE DERIVATIVES USING TRIFLUOROACETIC ACID AND DINITROGEN TETROXIDE

BACKGROUND OF THE INVENTION

Systematically, homonojirimycin is named 2,6-imino-2,6-dideoxy-D-glycero-L-e-heptitol; homonojirimycin glycosides have been described in U.S. Pat. No. 4,634,765 as inhibitors of carbohydrate digestive enzymes. The indicated compounds are prepared by the reaction of an appropriate protected homonojirimycin with a protected glycosyl halide followed by removal of the protecting groups. The indicated patent describes a multi-step procedure to prepare the necessary homonojirimycin starting materials; for the most part, the intermediates obtained in the various steps of the synthesis are not solid and it is necessary to use chromatography in the preparation and purification of some of these intermediates.

SUMMARY OF THE INVENTION

The present invention is directed to a new procedure for the preparation of the protected homonojirimycin starting materials referred to above. The new procedure provides an attractive alternative approach for obtaining the compounds because it generally avoids the use of chromatography in the preparation and purification procedures. Furthermore, depending on the particular protecting groups used, solid intermediates are obtained and such intermediates would be easier to handle in bulk quantities.

As part of the overall procedure, the present invention further includes a new procedure for the conversion of an electron-deficient carbonitrile to the corresponding carboxylic acid under mild reaction conditions and this procedure can be used generally with certain carbonitriles.

From an overall standpoint, the present invention is directed to a new process for accomplishing the following carbonitrile to carbinol conversion:

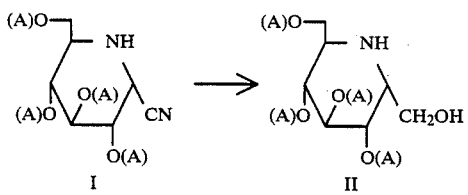

In the above formulas, (A) is alkanoyl containing 1-4 carbon atoms or benzoyl. The starting material in the above procedure is obtained by the reaction of the appropriate tetrahydroxypiperidine compound with an appropriate acid chloride. The product in the overall procedure above is shown as a free base and it can be isolated as such although the free base can readily be converted to a solid salt (strong acid) form by standard procedures using a strong acid. The free base or salt can then be reacted with benzyl chloroformate to give the corresponding N-benzyloxycarbonyl compound which can be converted to the ultimate desired glycosides by standard procedures. One such conversion is described in detail in U.S. Pat. No. 4,634,765 although some obvious modifications of the procedure may be necessary to take into account the fact that different protecting groups are used.

As indicated earlier, a significant aspect of the present process is a general procedure for the conversion of carbonitriles to carboxylic acids using mild reaction conditions. In this general procedure, a carbonitrile is first treated with trifluoroacetic acid, optionally in the presence of a catalytic amount of mercuric ion at room temperature, to give the corresponding carboxamide followed by oxidative hydrolysis of the carboxamide using dinitrogen tetroxide under some cooling to give the corresponding carboxylic acid. This procedure is applicable to electron deficient carbonitriles. The term "electron deficient carbonitrile" is used to describe carbonitriles containing an electron-withdrawing group in close enough proximity to the carbonitrile to have an electron-withdrawing effect on the nitrile. Examples of such compounds would be amides of α-aminocarbonitriles wherein the amide is derived from a strong acid such as trifluoroacetic acid; benzonitriles containing an electron-withdrawing group such as nitro at the 4-position; and 2-picolinonitrile. In contrast, benzoyl derivatives of α-aminocarbonitriles and benzonitrile itself are not affected by this hydrolysis procedure.

The homonojirimycin process, as shown in the equation above, can be summarized as follows. The carbonitrile (I) is reacted with trifluoroacetic anhydride to give the corresponding N-trifluoroacetyl compound (the amide of the ring nitrogen) also referred to as the 2,6-trifluoroacetylimino compound. The carbonitrile amide is then reacted at room temperature with trifluoroacetic acid optionally in the presence of a catalytic amount of mercuric ion followed by reaction with dinitrogen tetroxide to give the corresponding carboxylic acid. The resulting acid is treated with sodium borohydride, boron trifluoride and diborane and this treatment serves to hydrolyze the trifluoroacetic acid amide to the amine and reduce the carboxylic acid function to give the desired hydroxymethyl compound (II). The hydroxymethyl compound is then optionally reacted with a strong acid to give the corresponding amine salt.

In the procedure referred to above wherein the acid is treated with three different boron compounds, all three of the compounds are necessary in order to give the desired results consistently and the process is carried out using the three compounds separately. The exact order in which the three reagents are used can be varied although it appears preferable to use the borane first followed by the sodium borohydride and then the boron trifluoride. However, reaction with sodium borohydride first followed by boron trifluoride and then borane also gives satisfactory results.

In the starting material in the above procedure, the protecting groups (A) can be alkanoyl or benzoyl although benzoyl esters are preferred because they provide solid intermediates. Actually, when (A) is benzoyl in Formula II above, the product obtained is an oil but this can be readily converted to a corresponding solid amine salt by standard procedures.

The following examples are presented to illustrate the present invention. They should not be construed as limiting it in any way.

EXAMPLE 1

To a slurry of 50 g of 1α-cyano-1-deoxynojirimycin and 158 ml of triethyl amine in 1200 ml of ethyl acetate there was added 159 g of benzoyl chloride dropwise under nitrogen over a period of 40 minutes. The mixture was then allowed to stir at room temperature for 18 hours. The resulting cream-colored slurry was added to 2000 ml of a 1:1 mixture of ethyl acetate and water and mixed thoroughly before the two phases were allowed to form and were separated. The organic layer was washed successively with about 500 ml of brine, 500 ml of saturated aqueous sodium carbonate solution, and 500 ml of brine again and then dried over sodium sulfate. The solvents were evaporated from the organic extracts in vacuo to give a viscous oil which, upon trituration with 250 ml of cold methanol, provided a white solid. The solid was separated by filtration, washed with cold methanol, and dried in vacuo at about 60° C. for 5 hours to give 3,4,5,7-tetra-O-benzoyl-2,6-dideoxy-2,6-imino-D-glycero-D-ido-heptononitrile melting at about 179°–182° C. (81.7% yield).

EXAMPLE 2

To a stirred solution of 75 g of 3,4,5,7-tetra-O-benzoyl-2,6-dideoxy-2,6-imino-D-glycero-D-ido-heptononitrile and 17 ml of triethylamine in 1250 ml of ethyl acetate, cooled to 0° C. with an ice-water bath, there was added 49 ml of trifluoroacetic anhydride over a period of 20 minutes. The resulting solution was stirred at 0° C. for 1 hour and then allowed to warm to room temperature overnight. An additional 7 ml of trifluoroacetic anhydride was added and stirring was continued for 3 hours. The solution was poured into 1500 ml of ice-water and the resulting mixture was stirred vigorously for 1 hour. The layers were separated and the aqueous layer was extracted with 200 ml of ethyl acetate. The combined organic extracts were washed with 500 ml of brine and dried over anhydrous magnesium sulfate. Evaporation of the solvent in vacuo at below 45° C. gave an off-white solid. This material was triturated with 100 ml of cold methanol and the resulting solid was filtered, washed with cold methanol and air dried to give 3,4,5,7-tetra-O-benzoyl-2,6-dideoxy-2,6-[(trifluoroacetyl)imino]-D-glycero-D-ido-heptononitrile as a fine white powder melting at about 156°–159° C. (89.1% yield).

EXAMPLE 3

A solution of 76.8 g of 3,4,5,7-tetra-O-benzoyl-2,6-dideoxy-2,6-[(trifluoroacetyl)imino]-D-glycero-D-ido-heptononitrile and 5.1 g of mercuric trifluoroacetate in 280 ml of 90% trifluoroacetic acid was stirred at room temperature for 3.5 hours. The resulting pale-yellow solution was cooled to 5° C. with an ice-water bath and dinitrogen tetroxide was vigorously bubbled through the solution. During this process, evolution of fine-gas bubbles was noted. After 70 minutes, the dinitrogen tetroxide addition was stopped, the bath was removed, and stirring was continued for 1.5 hours. The yellow solution was then poured slowly into a vigorously stirred ice-water mixture (2500 ml). The solid which formed was separated by filtration and air dried to give 3,4,5,7-tetra-O-benzoyl-2,6-dideoxy-2,6-[(trifluoroacetyl)imino]-D-glyero-D-ido-heptonic acid as a fine-white powder melting at about 103°–113° C. (97.3% yield).

EXAMPLE 4A

To a stirred slurry of 4.8 g of sodium borohydride in 180 ml of tetrahydrofuran, cooled in an ice bath, there was added dropwise over a period of 20 minutes a solution of 60 g of 3,4,5,7-tetra-O-benzoyl-2,6-dideoxy-2,6-[(trifluoroacetyl)imino]-D-glycero-D-ido-heptonic acid in 180 ml of tetrahydrofuran. When gas evolution ceased, 3.6 ml of boron trifluoride etherate was added. After 2 hours, the ice bath was removed and 120 ml of 1.0M borane-tetrahydrofuran complex in tetrahydrofuran was added and the resulting solution was stirred for 16 hours. The pale-grey solution was cooled in an ice-water bath and 50 ml of methanol was added dropwise slowly. The mixture was allowed to warm to room temperature and the solvents were removed in vacuo. The resulting residue was dissolved in 700 ml of ethyl acetate and successively washed with 100 ml of 1N hydrochloric acid, two 100-ml portions of saturated aqueous sodium bicarbonate solution, and saturated aqueous sodium chloride solution and then dried over magnesium sulfate. Evaporation of the solvent gave a viscous orange oil which was crude 1,3,4,5-tetra-O-benzoyl-2,6-dideoxy-2,6-imino-D-glycero-L-gulo-heptitol which can be purified by chromatography. However, this residual oil was dissolved in 500 ml of ether and saturated ethereal hydrogen chloride was added dropwise with vigorous stirring until no additional precipitate formed. The resulting suspension was cooled and filtered; the filtrate obtained was refrigerated overnight and the resulting further precipitate was separated by filtration. The solids were combined to give 1,3,4,5-tetra-O-benzoyl-2,6-dideoxy-2,6-imino-D-glycero-L-gulo-heptitol hydrochloride as a cream-colored powder melting at about 209°–212° C. (61.8% yield).

Purification of the crude free amine as obtained above was carried out as follows. A 30 g portion of 1,3,4,5-tetra-O-benzoyl-2,6-dideoxy-2,6-imino-D-glycero-L-gulo-heptitol was dissolved in a minimum amount of dichloromethane and applied to a 5.0 cm (d) column of silica gel (130 g). The column was eluted with 2000 ml of dichloromethane and then with 500 ml of 2% acetone/dichloromethane. The fractions obtained by further elution with 5% acetone/dichloromethane contained most of the desired imino compound. The solvent was evaporated from the appropriate fractions to give 1,3,4,5-tetra-O-benzoyl-2,6-dideoxy-2,6-imino-D-glycero-L-gulo-heptitol as a pale-yellow oil.

EXAMPLE 4B

To a solution of 5.8 g of 3,4,5,7-tetra-O-benzoyl-2,6-dideoxy-2,6-[(trifluoroacetyl)imino]-D-glycero-D-ido-heptonic acid in 20 ml of tetrahydrofuran was added 12 ml of 1M borane in tetrahydrofuran over a period of 10 minutes. After stirring for 30 minutes, 1 g of sodium borohydride and 0.4 ml of boron trifluoride etherate were added successively to the mixture and the resulting solution was kept under nitrogen for 16 hours at room temperature. The mixture was cooled to 4° C. and 10 ml of methanol was added dropwise. The resulting mixture was stirred for another 30 minutes after the addition and then concentrated in vacuo to a residue. The residue was dissolved in 70 ml of ethyl acetate and washed with 20 ml of 1N hydrochloric acid, two 20-ml portions of aqueous sodium bicarbonate solution, and 20 ml of brine. The organic solution was dried over magnesium sulfate and the solvent was evaporated to leave an oily residue which was redissolved in 50 ml of anhydrous ether. The ethereal solution was added dropwise to a saturated solution of hydrogen chloride in 10 ml of ether and a cream-colored solid precipitated. The resulting slurry was cooled (0° C.) and stirred for 1 hour and the solid was separated by filtration to give 1,3,4,5-tetra-O-benzoyl-2,6-dideoxy-2,6-imino-D-glycero-L- gulo-heptitol hydrochloride melting at about 209°–211° C. (75% yield).

EXAMPLE 5

A solution of 32.2 g of 1,3,4,5-tetra-O-benzoyl-2,6-dideoxy-2,6-imino-D-glycero-L-gulo-heptitol hydrochloride in 250 ml of ethyl acetate was washed successively with two 200-ml portions of saturated aqueous sodium bicarbonate solution and saturated aqueous sodium chloride solution and then concentrated in vacuo. The residue was dissolved in 150 ml of tetrahydrofuran and 17.8 g of potassium carbonate was added. The resulting slurry was stirred and 11 ml of benzyl chloroformate was added dropwise. After 30 minutes, 30 ml of water was added and the stirred, two-phase mixture was warmed to 50° C.. After 2 hours, an additional 5 ml of benzyl chloroformate was added and heating was resumed for 1 hours. The cooled mixture was diluted with ethyl acetate and the two layers were separated. The organic layer was washed successively with saturated sodium bicarbonate solution, and saturated sodium chloride solution and then dried over anhydrous magnesium sulfate. Concentration of the solution gave a viscous pale-yellow oil. This residual oil was rinsed with hexane and then dissolved in a minimum amount of ether. The ethereal solution was refrigerated overnight and the solid which formed was isolated by filtration to give a cream-colored powder which was 1,3,4,5-tetra-O-benzoyl-2,6-dideoxy-2,6[[(phenylmethoxy)carbonyl]imino]-D-glycero-L-gulo-heptitol. The filtrate was concentrated and the residue was applied to a silica gel column and eluted with 30% ethyl acetate/hexane. The appropriate fractions were combined and concentrated in vacuo to give additional 1,3,4,5-tetra-O-benzoyl-2,6-dideoxy-2,6-[[(phenylmethoxy)carbonyl]imino]-D-glycero-L-gulo-heptitol as an off-white powder. This compound melts at about 145°–147° C. (overall yield, 75%).

EXAMPLE 6A

To a solution of 17.7 g of 1,3,4,5-tetra-O-benzoyl-2,6-dideoxy-2,6-[[(phenylmethoxy)carbonyl]imino]-D-glycero-L-gulo-heptitol in 200 ml of a 1:1 mixture of toluenenitromethane there was added 18 g of Molecular Sieve 4A, 10.6 g of acetobromoglucose and 7.1 g of mercuric cyanide. The mixture was stirred and warmed at 55° C. under nitrogen. Additional amounts of acetobromoglucose (5.3 g) and mercuric cyanide (3.55 g ) were added after 24 and 48 hours of reaction. After stirring for a total of 72 hours, the mixture was cooled, diluted with 200 ml of ethyl acetate and filtered through diatomaceous earth. The clear filtrate obtained was washed successively with 300 ml of saturated aqueous sodium bicarbonate solution, three 300-ml portions of saturated aqueous sodium bisulfite solution and 300 ml of brine. The organic solution was then dried over magnesium sulfate and the solvent evaporated in vacuo to give an oily residue which was redissolved in about 100 ml of methanol. The solution was cooled to 4° C., a seed crystal was added, and 1,3,4,5-tetra-O--benzoyl-2,6-dideoxy-2,6-[[(phenylmethoxy)carbonyl]imino]-7-O-(2,3,4,6-tetra-O-acetylβ-D-glucopyranosyl]-D-glycero-L-gulo-heptitol crystallized as a colorless solid melting at about 142°–144° C. (71% yield).

EXAMPLE 6B

To a cooled solution (−30° C.) of 185 g of 1,3,4,5-tetra-O-benzoyl-2,6-dideoxy-2,6-[[(phenylmethoxy)carbonyl]imino]-D-glycero-L-gulo-heptitol and 202 g 2,3,4,6-tetra-O-acetyl-β-D-glucopyranosyl trichloroacetimidate in 400 ml of dichloromethane was added 40 ml of boron trifluoride etherate over a period of 5 minutes. After stirring for 1.5 hours at −20° C., the mixture was diluted with 300 ml of dichloromethane and added to 300 ml of aqueous sodium bicarbonate solution. The organic phase was separated and washed with saturated aqueous sodium bicarbonate solution (2×300 ml) and 300 ml of brine and dried over magnesium sulfate. Evaporation of the solvent from the extract gave an oily residue which was redissolved in 740 ml of methanol at 60° C.. Upon cooling overnight, the crude product crystallized as a colorless solid and was collected by filtration. The solid was washed successively with 500 ml of cold methanol and with 500 ml of ether to give 1,3,4,5-tetra-O-benzoyl-2,6-dideoxy-2,6-[[(phenylmethoxy)carbonyl]imino]-7-O-(2,3,4,6-tetra-O-acetyl-β-D-glucopyranosyl]-D-glycero-L-gulo-heptitol melting at about 141°–142° C. (85% yield).

EXAMPLE 7

To a stirred suspension of 52 g of 1,3,4,5-tetra-O-benzoyl-2,6-dideoxy-2,6-[[(phenylmethoxy)carbonyl-]imino]7-O-(2,3,4,6-tetra-O-acetyl-β-D-glucopyranosyl]-D-glycero-L-gulo-heptitol and 400 ml of methanol under nitrogen there was added a suspension of 2.5 g of 10% Pd/C in 10 ml of ethanol followed by 100 ml of cyclohexene. The mixture was stirred and warmed at 60° C. for 4 hours. It was then cooled and filtered through diatomaceous earth and the solvent was evaporated to give a foamy residue. The residue was dissolved in 350 ml of methanol and, after the addition of 10 drops of 4.4M sodium methoxide in methanol, the mixture was stirred at room temperature under nitrogen for 18 hours. An additional 10 drops of sodium methoxide in methanol was added and stirring was continued for another 24 hours. The colorless crystals which separated out from the methanolic solution were collected and washed with a cold 1:1 mixture of acetone-methanol. The crystals were dried in vacuo at 45° C. to give 2,6-imino-2,6-dideoxy-7-O-(β-D-glucopyranosyl)-D-glycero-L-gulo-heptitol melting at about 216°–219° C. (84% yield).

EXAMPLE 8

To a well-stirred suspension of 3.0 g of 1α-cyano-1-deoxynojirimycin and about 25 mg of 4-dimethylaminopyridine in 35 ml of ethyl acetate there was added 12.0 g of acetic anhydride in one portion at room temperature. The resulting thin, cream-colored slurry was heated to reflux and refluxed for 18 hours. The stirred mixture was then cooled to 50° C. and 25 ml of water was added in one portion. The resulting mixture was allowed to stir and cool to room temperature and then diluted with 25 ml of ethyl acetate. A solution of 12.0 g of sodium bicarbonate in 50 ml of water was then added carefully. After thorough mixing, the ethyl acetate layer was separated and the aqueous layer was further extracted with two 30-ml portions of ethyl acetate. The combined organic solutions were washed with 50 ml of 10% aqueous sodium bicarbonate solution and then 50 ml of brine and dried over sodium sulfate. Evaporation of the solvent in vacuo left crude product which solidified. Purification by chromatography over 110 g of silica using 5% acetone in dichloromethane as eluent gave purified product which was recrystallized from 1:1 ethyl acetate/hexane to give 3,4,5,7-tetra-O-acetyl-2,6-dideoxy-2,6-imino-D-glycero-D-ido-heptononitrile as fine white needles melting at about 163°–164° C.

EXAMPLE 9

The procedure of Example 2 was repeated using trifluoroacetic anhydride and 2.5 g of 3,4,5,7-tetra--O-acetyl-2,6-dideoxy-2,6-imino-D-glycero-D-ido-heptononitrile. In this case, evaporation of the solvent from the extracts of the reaction mixture gave a thick viscous oil which was 3,4,5,7-tetra-O-acetyl-2,6-dideoxy-2,6-[(trifluoroacetyl)-imino]-D-glycero-D-ido-heptononitrile.

EXAMPLE 10

The 3,4,5,7-tetra-O-acetyl-2,6-dideoxy-2,6-[(trifluoroacetyl)imino]-D-glycero-D-ido-heptononitrile obtained in Example 9 is first reacted with mercuric trifluoroacetate in trifluoro-acetic acid and then with dinitrogen tetroxide, both according to the procedure described in Example 3, to give 3,4,5,7-tetra-O-acetyl-2,6-dideoxy-2,6-[(trifluoroacetyl)imino]-D-glycero-D-ido-heptonic acid. This acid is then reduced using sodium borohydride in tetrahydrofuran according to the procedure described in Example 4A to give 1,3,4,5-tetra-O-acetyl-2,6-dideoxy-2,6-imino-D-glycero-L-gulo-heptitol. The isolation procedures involved are modified to take into account the fact that the products obtained are oils rather than solids.

What is claimed is:

1. A process for converting an electron deficient carbonitrile to a carboxylic acid, said electron deficient carbonitrile being an amide of a 2,6-dideoxy-2,6-iminoheptononitrile wherein the amide is derived from a strong acid, which comprises treating the carbonitrile with trifluoroacetic acid followed by oxidative hydrolysis with dinitrogen tetroxide.

2. A process according to claim 1 wherein the carbonitrile is 3,4,5,7-tetra-O-benzoyl-2,6-[(trifluoroacetyl)imino]-D-glycero-D-ido-o-heptononitrile and the carboxylic acid is 3,4,5,7-tetra-O--benzoyl-2,6-dideoxy-2,6-[(trifluoroacetyl)imino]-D-glycero-D-ido-heptonic acid.

3. A process for converting a 3,4,5,7-tetra-O-(A)2,6-dideoxy-2,6-imino-D-glycero-D-ido-heptononitrile wherein A is alkanoyl of 1–4 carbon atoms or benzoyl to 1,3,4,5-tetra-O-(A)-2,6-dideoxy-2,6-imino-D-glycero-L-gulo-heptitol which comprises reacting the heptononitrile with trifluoroacetic anhydride to give the corresponding 2,6-trifluoroacetylimino compound; reacting this compound with trifluoroacetic acid followed by reaction with dinitrogen tetroxide to give the corresponding heptonic acid; followed by treatment with borane, sodium borohydride and boron trifluoride to give the desired heptitol.

4. A process according to claim 3 for converting a 3,4,5,7-tetra-O-benzoyl-2,6-dideoxy-2,6-imino-D-glycero-D-ido-heptononitrile to 1,3,4,5-tetra-O-benzoyl-2,6-dideoxy-2,6-imino-D-glycero-L-gulo-heptitol which comprises reacting the heptononitrile with trifluoroacetic anhydride to give the corresponding 2,6-trifluoroacetylimino compound; reacting this compound with trifluoroacetic acid in the presence of a catalytic amount of mercuric ion followed by reaction with dinitrogen tetroxide to give the corresponding heptonic acid; followed by treatment with borane, sodium borohydride and boron trifluoride to give the desired heptitol.

5. A process according to claim 1 wherein the treatment of the carbonitrile with trifluoroacetic acid is carried out in the presence of a catalytic amount of mercuric ion.

* * * * *

UNITED STATES PATENT AND TRADEMARK OFFICE
CERTIFICATE OF CORRECTION

PATENT NO. : 4,880,917
DATED : November 14, 1989
INVENTOR(S) : Peter B. Anzeveno, John K. Daniel, Laura J. Creemer and Paul S. Liu It is certified that error appears in the above-identified patent and that said Letters Patent is hereby corrected as shown below:

Column 1, line 10, "-L-e-heptitol" should read -- -L-gulo-heptitol --.

Column 2, line 4 & 5, "of carbonitriles" should read -- of electron-deficient carbonitriles --.

Column 2, line 29, "nitrogen) also ... compound" should read -- nitrogen; also referred to as 2,6-trifluroroacetylimino compound) --.

Column 3, line 59, "glyero" should read -- glycero --.

Column 5, line 65, "-acetylβ should read -- -acetyl-β --.

Column 6, line 6, " -acetyl-β should read -- -acetyl-α- --.

Column 8, line 5, "-D-ido-o-heptononitrile" should read -- -D-ido-heptononitrile --.

Signed and Sealed this

Eleventh Day of December, 1990

Attest:

HARRY F. MANBECK, JR.

Attesting Officer

Commissioner of Patents and Trademarks